US011333732B2

(12) United States Patent
Sommer et al.

(10) Patent No.: US 11,333,732 B2
(45) Date of Patent: May 17, 2022

(54) AUTOMATIC ARTIFACT DETECTION AND PULSE SEQUENCE MODIFICATION IN MAGNETIC RESONANCE IMAGING

(71) Applicant: KONINKLIJKE PHILIPS N.V., Eindhoven (NL)

(72) Inventors: Karsten Sommer, Hamburg (DE); Axel Saalbach, Hamburg (DE); Michael Gunter Helle, Hamburg (DE); Steffen Weiss, Hamburg (DE); Christophe Michael Jean Schulke, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/047,749

(22) PCT Filed: Apr. 17, 2019

(86) PCT No.: PCT/EP2019/059872
§ 371 (c)(1),
(2) Date: Oct. 15, 2020

(87) PCT Pub. No.: WO2019/201968
PCT Pub. Date: Oct. 24, 2019

(65) Prior Publication Data
US 2021/0156940 A1 May 27, 2021

(30) Foreign Application Priority Data

Apr. 19, 2018 (EP) ..................................... 18168248

(51) Int. Cl.
*G01V 3/00* (2006.01)
*G01R 33/54* (2006.01)
(Continued)

(52) U.S. Cl.
CPC ............ *G01R 33/543* (2013.01); *A61B 5/055* (2013.01); *G01R 33/565* (2013.01); *G01R 33/5608* (2013.01); *A61B 5/7207* (2013.01)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 5,339,818 A * 8/1994 Baker ................ A61B 5/02156
600/490
6,501,849 B1 12/2002 Gupta et al.
(Continued)

OTHER PUBLICATIONS

Krupa, K. et al., "Artifacts In Magnetic Resonance Imaging" Pol J Radiol, 80:93-106, 2015.
(Continued)

*Primary Examiner* — Walter L Lindsay Jr.
*Assistant Examiner* — Frederick Wenderoth

(57) ABSTRACT

The invention provides for a magnetic resonance imaging system (100, 300). The execution of machine executable instructions causes a processor (130) controlling the magnetic resonance imaging system to control (200) the magnetic resonance imaging system to acquire the magnetic resonance imaging data (144) using pulse sequence commands (142) and reconstruct (202) a magnetic resonance image (148). Execution of the machine executable instructions causes the processor to receive (204) a list of suggested pulse sequence command changes (152) by inputting the magnetic resonance image and image metadata (150) into an MRI artifact detection module (146, 146', 146"). The MRI artifact detection module comprises at least one neural network, which has been trained using images from failed magnetic resonance imaging protocols and/or magnetic resonance data extracted from the magnetic resonance imag-
(Continued)

ing protocols labeled as failed accessed from a log file (312) which logs the execution of previous magnetic resonance imaging protocols. Execution of the machine executable instructions further causes the processor to receive (206) a selection of a chosen pulse sequence command change (158) from the list of suggested pulse sequence command changes. Execution of the machine executable instructions further causes the processor to modify (208) the pulse sequence commands using the chosen pulse sequence command change.

20 Claims, 7 Drawing Sheets

(51) Int. Cl.
  *A61B 5/055* (2006.01)
  *G01R 33/56* (2006.01)
  *G01R 33/565* (2006.01)
  *A61B 5/00* (2006.01)

(58) Field of Classification Search
  USPC .......................................................... 324/309
  See application file for complete search history.

(56) References Cited

U.S. PATENT DOCUMENTS

| | | | | |
|---|---|---|---|---|
| 9,569,060 | B2* | 2/2017 | Al-Alami | G06F 3/0483 |
| 9,612,723 | B1* | 4/2017 | Elliot | G06F 3/0482 |
| 2008/0139921 | A1* | 6/2008 | Biglieri | A61B 5/055 |
| | | | | 600/410 |
| 2009/0006131 | A1 | 1/2009 | Unger et al. | |
| 2010/0204973 | A1* | 8/2010 | Parkinson | G16B 50/30 |
| | | | | 703/11 |
| 2011/0110572 | A1 | 5/2011 | Guehring et al. | |
| 2011/0210734 | A1 | 9/2011 | Darrow et al. | |
| 2012/0010495 | A1 | 1/2012 | De Oliveira et al. | |
| 2012/0089008 | A1* | 4/2012 | Strehl | G01R 33/286 |
| | | | | 600/411 |
| 2014/0010432 | A1 | 1/2014 | Cohen-Solal et al. | |
| 2014/0221832 | A1 | 8/2014 | El-Zehiry et al. | |
| 2015/0115963 | A1* | 4/2015 | Huang | G01R 33/283 |
| | | | | 324/322 |
| 2015/0362566 | A1 | 12/2015 | Haider et al. | |
| 2017/0011185 | A1 | 1/2017 | Schweizer | |
| 2017/0027464 | A1* | 2/2017 | Cole | A61B 5/7207 |
| 2017/0351937 | A1 | 12/2017 | Lu et al. | |
| 2018/0100907 | A1 | 4/2018 | Soza et al. | |

OTHER PUBLICATIONS

M. Zaitsev, et al., "Motion Artifacts in MRI: A Complex Problem with Many Partial Solutions" JMRI 42:887-901, 2015.

Morelli, J. N. et al., "An Image Based Approach to Understanding the Physics of MR Artifacts" Radiographics, 31 (3):849-866, 2011.

S. Hey et al., Orthopedic metal artifact reduction in MRI, Philips White paper, 2016.

Pipe J.G. et al., "Revised Motion Estimation Algorithm for Propeller MRI" Magn Reson Med 72(2):430-7, 2014.

A. Krizhevsky, et al.,"ImageNet Classification with Deep Convolutional Neural Networks" Adv Neural Inf Process Syst, 2012.

Stocker T. et al., "High Performance Computing MRI Simulations" Magn Reson Med 64(1):186-193, 2010.

International Search Report and Written Opinion from PCT/EP2019/059872 dated Jun. 26, 2019.

Kustner Thomas et al: "Automated reference-free detection of motion artifacts in magnetic resonance images", Magnetic Resonance Materials in Physics, Biology and Medicine, Springer, DE, GB, vol. 31, No. 2, Sep. 20, 2017 (Sep. 20, 2017), pp. 243-256.

* cited by examiner

AUTOMATIC ARTIFACT DETECTION AND PULSE SEQUENCE MODIFICATION IN MAGNETIC RESONANCE IMAGING

CROSS REFERENCE TO RELATED APPLICATIONS

This application is a U.S. national phase application of International Application No. PCT/EP2019/059872 filed on Apr. 17, 2019, which claims the benefit of EP Application Serial No. 18168248.5 filed on Apr. 19, 2018 and is incorporated herein by reference.

FIELD OF THE INVENTION

The invention relates to magnetic resonance imaging, in particular to reduction of artifacts during magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a subject. This large static magnetic field is referred to as the BO field or the main magnetic field. Various quantities or properties of the subject can be measured spatially using MRI. However, the acquisition of a magnetic resonance imaging data is not instantaneous and voluntary and/or involuntary subject motion can cause artifacts or anomalies with the magnetic resonance image. Additionally, incorrectly configuring the magnetic resonance imaging system or the presence of metallic implants with the subject can also cause anomalies within the magnetic resonance image. Among the most common problems are motion artifacts caused by bulk subject movement, cardiac motion, or blood flow, aliasing artifacts due to improper scan planning, signal voids due to magnetic materials in the patient, geometric distortion caused by field inhomogeneity, and chemical shift artifacts United States patent application publication US 2011/0110572 A1 discloses a system that dynamically improves quality of medical images using at least one processing device including an image analyzer, a correction processor and a message generator. The image analyzer automatically parses and analyzes data representing an image of a particular anatomical feature of a patient acquired by a medical image acquisition device to identify defects in the image by examining the data representing the image for predetermined patterns associated with image defects. The correction processor uses a predetermined information map associating image defects with corresponding corrective image acquisition parameters to determine corrected image acquisition parameters for use in reacquiring an image using the image acquisition device in response to an identified defect. The message generator generates a message for presentation to a user indicating an identified defect and suggesting use of the corrected image acquisition parameters for reacquiring an image.

SUMMARY OF THE INVENTION

The invention provides for a magnetic resonance imaging system, a method, and a computer program product in the independent claims. Embodiments are given in the dependent claims.

Embodiments of the invention provide for a means of reducing artifacts in magnetic resonance images by using a MRI artifact detection module that comprises at least one neural network. The MRI artifact detection module identifies artifacts in a magnetic resonance image and provides a list of suggested pulse sequence command changes. That is, the magnetic resonance image with its metal data is input the MRI artifact detection module. The MRI artifact detection module in configured in software to recognise and identify image artifacts in the magnetic resonance image. The MRI artifact detection module's trained neural network functions as an artifact classifier outputting an artifact classification of the input. magnetic resonance image the list of suggested pulse sequence command changes. One of the list of suggested pulse sequence command changes may be used to modify the pulse sequence commands. The modified pulse sequence commands can for example be used to reacquire the magnetic resonance image. When a series of magnetic resonance images are being acquired, the modified pulse sequence commands can also be used to correct and improve the quality of subsequently acquired magnetic resonance image.

The MRI artifact detection module may be incorporated in the software architecture of the magnetic resonance image system, that is the MRI artifact detection module is incorporate in the computer system that controls the magnetic resonance imaging system. Alternatively, the MRI artifact detection module, as well as the reconstruction module may be configured in software that may be located remotely and is accessible by the magnetic resonance imaging system. Thus, the functions of the MRI artefact detection module may be performed remotely. This remote performance may be done at a central server accommodating several magnetic resonance imaging systems within a healthcare institution. Even, the remote performance of the MRI artifact detection module may take place on-line from The Cloud. Also image reconstruction may be done remotely, e.g. from The Cloud. The at least one neural network and other neural networks referred to herein may in some cases be Convolutional Neural Networks. The training of neural networks referred to herein may in some cases be performed using an optimizing algorithm. In some examples, the arrangement for automatic artefact detection therefore makes use of a convolutional neural network (CNN) and deep learning. The CNN may possibly be trained from artefact-corrupted magnetic resonance images with corresponding labels that mention the type of artefact and a likely MR technique to avoid this artefact. This training may possibly be done from labelled images that are collected on the fly by regularly enquiring with experienced radiologist when an artefact is noted in the magnetic resonance image if the alternative MR technique has solved the issue. This training build-up may run in the background of regular imaging protocols. Training data may also be acquired from the system log-files by noting repeated scans and analyzing that situation for artefact type and how that was resolved. In some implementations the CNN may provide a probability score (or an image improvement likelihood score) for the alternative MR technique to be successful. That is, the image improvement likelihood score associated with a pulse sequence command change represents the probability that the change of the pulse sequence will reduce the artifact level of the magnetic resonance image reconstructed from magnetic resonance signals acquired with the changed pulse sequence. The CNN may also analyze images in a series and provide a recommendation if and how to continue the acquisition of a series of images after corruption have been identified in the first (fewer) images in the series. Some embodiments may therefore improve the imaging workflow in that artefacts are timely identified and properly corrected for. This may help avoid or reduce the need for extensive re-scanning of the subject.

In one aspect the invention provides for a magnetic resonance imaging system configured for acquiring magnetic resonance imaging data from a subject. The magnetic resonance imaging data may be acquired from an imaging zone generated by a magnet of the magnetic resonance imaging system. The magnetic resonance imaging system comprises a memory for storing machine-executable instructions and pulse sequence commands. The pulse sequence commands are configured for controlling the magnetic resonance imaging system to acquire the magnetic resonance imaging data according to a magnetic resonance imaging protocol. Pulse sequence commands as used herein encompass commands or data which may be compiled or constructed into such commands that are used to control the operation and function of the magnetic resonance imaging system. Sometimes pulse sequence commands take the form of a timing diagram which indicates what operations are performed by which component of the magnetic resonance imaging system.

The magnetic resonance imaging system further comprises a processor configured for controlling the magnetic resonance imaging system. Execution of the machine-executable instructions causes the processor to control the magnetic resonance imaging system to acquire the magnetic resonance imaging data using the pulse sequence commands. Execution of the machine-executable instructions further causes the processor to reconstruct a magnetic resonance image using the magnetic resonance imaging data.

Execution of the machine-executable instructions further causes the processor to receive a list of suggested pulse sequence command changes by inputting the magnetic resonance image and image metadata into an MRI artifact detection module. The MRI artifact detection module comprises at least one neural network. The image metadata comprises pulse sequence parameters selected from the pulse sequence commands. Each of the suggested pulse sequence command changes comprises an image improvement likelihood score. The image improvement likelihood score may in some instances be a probability or other number which indicates the likelihood that a particular suggested pulse sequence command change will improve the quality or reduce anomalies in the magnetic resonance image. Execution of the machine-executable instructions further causes the processor to receive a selection of a chosen pulse sequence command change from the list of suggested pulse sequence command changes. Execution of the machine-executable instructions further causes the processor to modify the pulse sequence commands using the chosen pulse sequence command change.

In one embodiment the at least one neural network is at least one convolution neural network.

In some examples the modification of the pulse sequence commands could be minor such as changing a few parameters such as a repetition time or the modification of a flip angle. In other examples the modification of the pulse sequence commands could be major such as replacing the imaging protocol with a different imaging protocol.

The pulse sequence parameters are data which is descriptive of the magnetic resonance imaging protocol being used for imaging. The pulse sequence parameters may include such information as the region of interest, the type of anatomy being imaged, the type of pulse sequence being used, and also individual parameters used within a pulse sequence.

In some examples the receiving of the selection of the chosen pulse sequence command changes from the list of suggested pulse sequence command changes may be performed automatically or may be received manually from a user of the magnetic resonance imaging system. For example, the machine-executable instructions could be programmed to select the chosen pulse sequence command change using a predetermined criterion and the image improvement likelihood score.

In another embodiment execution of the machine-executable instructions further cause the processor to display a review prompt and the magnetic resonance image on the user interface. The review prompt displays an artifact type listing. Execution of the machine-executable instructions further cause the processor to receive a selection from the artifact type listing. Execution of the machine-executable instructions further cause the processor to train the parameters of the at least one neural network using the selection from the artifact type listing. This embodiment may be beneficial because it may provide for automated training of the MRI artifact detection module as it is being used.

In another embodiment the at least one neural network is trained using deep learning. Other references herein to the training of neural networks may be performed using an optimizing algorithm.

In another embodiment the at least one neural network is trained using deep learning. Other references herein to the training of neural networks may be performed using deep learning.

In another embodiment execution of the machine-executable instructions further causes the processor to provide a localization marking tool on the review prompt for the magnetic resonance image. The localization marking tool may for example be an object on the user interface which is used to indicate at least a portion of the location in the image of where the artifact is. For example, the localization marking tool may comprise a tool for indicating a segmentation of the image, a bounding box, or a central location of the artifact. Execution of the machine-executable instructions further cause the processor to receive a localization selection indicating at least a portion of the magnetic resonance image. The MRI artifact detection module is further configured for outputting an artifact location indicator. Execution of the machine-executable instructions further cause the processor to train the at least one neural network to generate the artifact location indicator using the localization selection.

Execution of the machine-executable instructions further cause the processor to train the at least one neural network to generate the artifact location indicator using the localization selection. Execution of the machine-executable instructions further cause the processor to receive the artifact location indicator from the MRI artifact detection module in response to the magnetic resonance image and the image metadata. Execution of the machine-executable instructions further cause the processor to display the magnetic resonance image on the warning prompt. Execution of the machine-executable instructions further cause the processor to display the artifact location indicator superimposed on the magnetic resonance image on the warning prompt. This embodiment may be beneficial because the addition of the artifact location indicator may improve the ability of an operator to identify an artifact in the magnetic resonance image.

In another embodiment execution of the machine-executable instructions further causes the processor to record manual changes in the pulse sequence commands if acquisition of the magnetic resonance imaging data is manually repeated. Execution of the machine-executable instructions further cause the processor to receive an image quality rating descriptive of a repeated magnetic resonance image reconstructed from the manually repeated magnetic resonance imaging data. Execution of the machine-executable instructions further causes the processor to train the at least one neural network using the manual changes in the pulse sequence commands if the image quality rating is above a predetermined threshold. This embodiment may be beneficial because as an operator manually reconfigures the magnetic resonance imaging system to improve image quality the system will learn how to do this automatically.

In another embodiment the memory stores a log file which logs execution of the previous magnetic resonance imaging protocols. Execution of the machine-executable instructions further cause the processor to search the log file for magnetic resonance imaging protocols labeled as failed. Execution of the machine-executable instructions further causes the processor to train the at least one neural network using images from the failed magnetic resonance imaging protocols and/or magnetic resonance data extracted from the magnetic resonance imaging protocols labeled as failed. In some examples a review prompt as disclosed above may also be displayed as part of the training process. This embodiment may be beneficial because it may provide a means for retrospectively looking at magnetic resonance data acquired by the magnetic resonance imaging system and using it to further train the at least one neural network.

In another embodiment execution of the machine-executable instructions further causes the processor to receive subject data descriptive of the subject. The training is supplemented using the subject data. The image metadata comprises the subject data. The subject data may for example be descriptive of a physical condition of the subject. The subject data may include such information as the age, size, the medical status, the possible presence of implants within the subject, as well as the image quality ratings of previous exams of the same patient. This embodiment may be beneficial because it may provide for a means of improving the identification of artifacts in magnetic resonance images.

In another embodiment execution of the machine-executable instructions further causes the processor to receive system data descriptive of a state and/or configuration of the magnetic resonance imaging system. The training is supplemented using the system data. The image metadata comprises the system data. This embodiment may be beneficial because certain configurations of the magnetic resonance imaging system may increase or reduce the probability of obtaining a magnetic resonance image within an image artifact.

In another embodiment the at least one neural network is a single neural network. This embodiment may be beneficial because the entire MRI artifact detection module is implemented as a single neural network. This may be implemented in several different ways, for example the image metadata might be clustered into a few distinct classes and then the network may be trained for each of these classes.

In another embodiment the single neural network comprises at least one fully connected layer. The image metadata is input into the at least one fully connected layer. This embodiment may be beneficial because it provides for an efficient means of integrating the input of the image metadata into the single neural network.

In another embodiment the MRI artifact detection module comprises an artifact classifier. The artifact classifier is a first neural network. The at least one neural network comprises the first neural network. The first neural network is configured to output an artifact classification of the magnetic resonance image in response to inputting the magnetic resonance image. The MRI artifact detection module further comprises a pulse sequence modification module configured to output the list of suggested pulse sequence command changes in response to the artifact classification and the pulse sequence parameters selected from the pulse sequence commands. This embodiment may be beneficial because the neural network may be used to effectively identify the artifact and then other means may be used to provide the list of suggested pulse sequence command changes.

The pulse sequence modification module may for example be any one of the following: a second neural network, an expert system, and a statistical learning module. This embodiment may be beneficial because it may provide for various means of providing the list of suggested pulse sequence command changes.

In another embodiment the memory comprises an MRI artifact detection module database comprising multiple MRI artifact detection modules. The multiple MRI artifact detection modules comprise the MRI artifact detection module. Execution of the machine-executable instructions further causes the processor to select the MRI artifact detection module using the magnetic resonance imaging protocol. This embodiment may be beneficial because there may be an MRI artifact detection module that has been trained for each of a particular class of magnetic resonance imaging protocols. The magnetic resonance imaging protocols may be divided in different ways. For example, the type of pulse sequence may be used to differentiate how the MRI artifact detection module is selected. In other examples the particular anatomy being imaged may be used as a selection. For example, there may be one MRI artifact detection module that is used when imaging knees and another when the brain is imaged. This may be beneficial because the characteristics of the images may be different.

In another embodiment execution of the machine-executable instructions further causes the processor to reacquire the magnetic resonance imaging data after modifying the pulse sequence commands using the chosen pulse sequence command change. Execution of the machine-executable instructions further cause the processor to reconstruct the magnetic resonance image using the reacquired magnetic resonance imaging data. This embodiment may be beneficial because it may provide for a means of providing improved magnetic resonance images.

In another embodiment the pulse sequence commands are configured for acquiring a series of magnetic resonance images. Execution of the machine-executable instructions further causes the processor to resume acquisition of the series of magnetic resonance images after modifying the pulse sequence commands using the chosen pulse sequence command change. In this embodiment the quality of a series of magnetic resonance images is improved by modifying them with the chosen pulse sequence command change.

In another embodiment the selection criteria is received from a selection module that is configured to select the chosen pulse sequence commands using a predetermined criteria applied to the image improvement likelihood score. That is, e.g. the selection of the chosen pulse sequence command change is made on the basis of the image improvement likelihood score of the pulse sequence command change. In other words, the pulse sequence command may be changed to a changed pulse sequence command that has a higher, or even the highest image improvement likelihood score. Thus, the changed pulse sequence is highly likely to lead to reduction of the artifact level of the magnetic resonance image. This embodiment may be beneficial because it may provide for an automated improvement of magnetic resonance images. In another embodiment execution of the machine-executable instructions further cause the processor to display a warning prompt on the user interface. The warning prompt may be displayed if at least one image improvement likelihood score is above a predetermined threshold. The warning prompt displays a list of the suggested pulse sequence command changes. The selection of the chosen pulse sequence command changes is received from the user interface. This embodiment may be beneficial because it may provide for a means for an operator to manually improve the magnetic resonance images.

The display of the list of suggested pulse sequence command changes may be done in different ways in different examples. In some cases, the list of suggested pulse sequence command changes are ranked using the image improvement likelihood score. In some examples the image improvement likelihood score is displayed along with each of the elements of the list of the suggested pulse sequence command changes. This may provide a means to facilitate the selection of the preferred chosen pulse sequence command change.

In another aspect, the invention provides for a computer program product comprising machine executable instructions for execution by a processor. Execution of the machine executable instructions causes the processor to receive a magnetic resonance image. Execution of the machine executable instructions further causes the processor to receive image metadata comprising pulse sequence parameters selected from pulse sequence commands. Execution of the machine executable instructions further causes the processor receive a list of suggested pulse sequence command changes by inputting the magnetic resonance image and image metadata into an MRI artifact detection module. The MRI artifact detection module comprises at least one neural network. Each of the suggested pulse sequence command changes comprises an image improvement likelihood score. The advantages of this embodiment have been previously discussed. This embodiment could for example be used as add on software or a plugin for machine executable instructions that control a magnetic resonance imaging system.

In another embodiment, execution of the machine-executable instructions further causes the processor to receive a selection of a chosen pulse sequence command change from the list of suggested pulse sequence command changes. Execution of the machine-executable instructions further causes the processor to modify the pulse sequence commands using the chosen pulse sequence command change.

In another aspect the invention provides for a computer program product comprising machine-executable instructions for execution by a processor controlling a magnetic resonance imaging system that is configured for acquiring magnetic resonance imaging data from a subject within an imaging zone. Execution of the machine-executable instructions causes the processor to control the magnetic resonance imaging system to acquire the magnetic resonance imaging data using pulse sequence commands. The pulse sequence commands are configured for controlling the magnetic resonance imaging system to acquire the magnetic resonance imaging data according to a magnetic resonance imaging protocol.

Execution of the machine-executable instructions further causes the processor to reconstruct a magnetic resonance image using the magnetic resonance imaging data. Execution of the machine-executable instructions further causes the processor to receive a list of suggested pulse sequence command changes by inputting the magnetic resonance image and image metadata into a magnetic resonance imaging artifact detection module. The MRI artifact detection module comprises at least one neural network. The image metadata comprises pulse sequence parameters selected from the pulse sequence commands. Each of the suggested pulse sequence command changes comprises an image improvement likelihood score. Execution of the machine-executable instructions further causes the processor to receive a selection of a chosen pulse sequence command change from the list of suggested pulse sequence command changes. Execution of the machine-executable instructions further causes the processor to modify the pulse sequence commands using the chosen pulse sequence command change. The advantages of this embodiment have been previously discussed.

In another aspect the invention provides for a method of operating a magnetic resonance imaging system configured for acquiring magnetic resonance imaging data from a subject. The subject is within the imaging zone. The method comprises controlling the magnetic resonance imaging system to acquire the magnetic resonance imaging data using the pulse sequence commands. The pulse sequence commands are configured for controlling the magnetic resonance imaging system to acquire the magnetic resonance imaging data according to a magnetic resonance imaging protocol. The method further comprises reconstructing a magnetic resonance image using the magnetic resonance imaging data.

The method further comprises receiving a list of suggested pulse sequence command changes by inputting the magnetic resonance image and image metadata into an MRI artifact detection module. The MRI artifact detection module comprises at least one neural network. The image metadata comprises pulse sequence parameters selected from the pulse sequence commands. Each of the suggested pulse sequence command changes comprises an image improvement likelihood score. The method further comprises receiving a selection of a chosen pulse sequence command change from the list of suggested pulse sequence command changes. The method further comprises modifying the pulse sequence commands using the chosen pulse sequence command change. The advantages of this embodiment have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance Imaging (MRI) data is defined herein as being the recorded measurements of radio frequency signals emitted by atomic spins using the antenna of a Magnetic resonance apparatus during a magnetic resonance imaging scan. A Magnetic Resonance image or MR image is defined herein as being the reconstructed two or three-dimensional visualization of anatomic data contained within the magnetic resonance imaging data. This visualization can, for example, be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
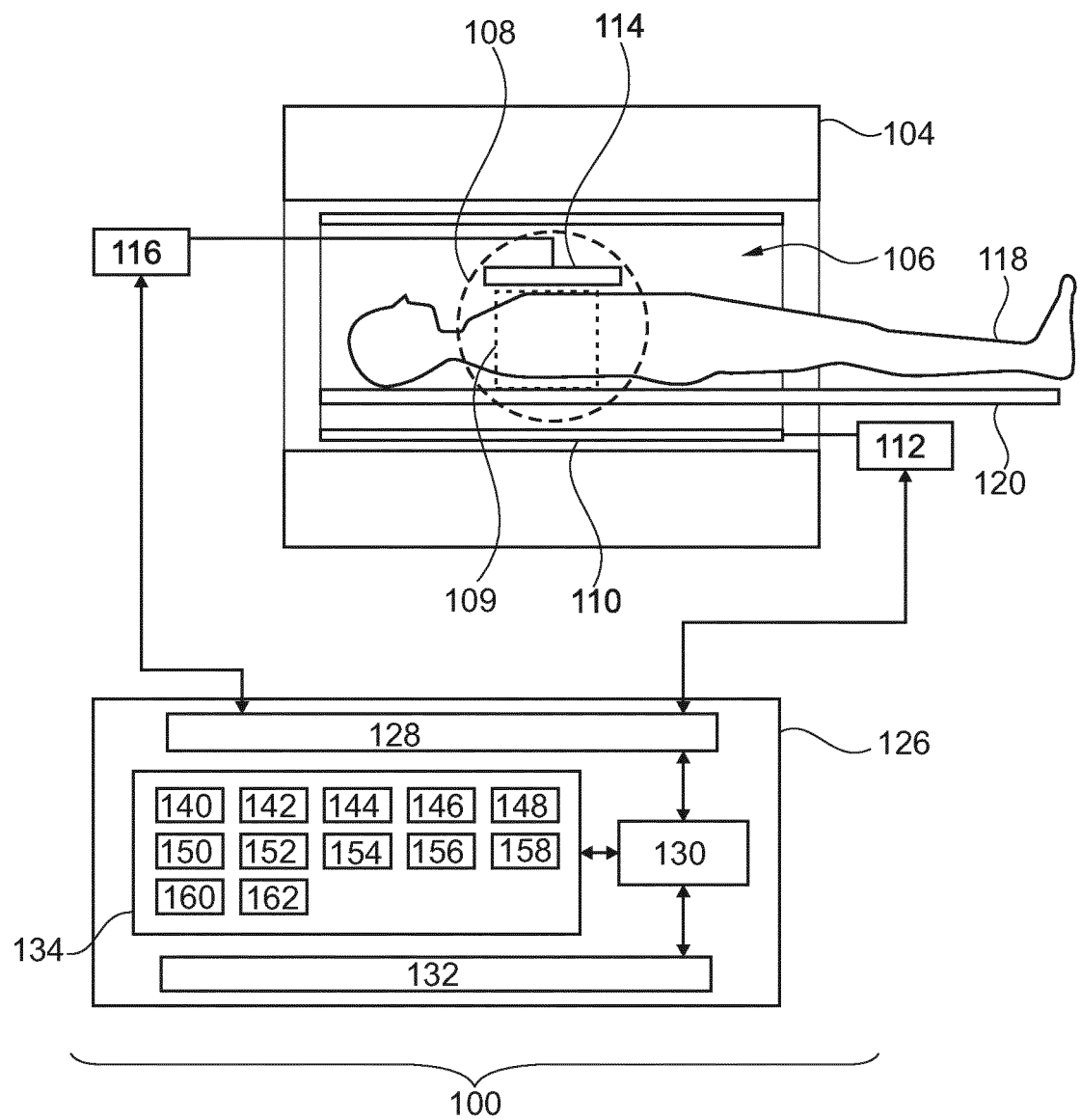
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. The magnetic resonance data that is acquired typically acquired for the region of interest. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

The transceiver 116 and the gradient controller 112 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 134 may be considered to be a non-transitory computer-readable medium.

The memory 134 is shown as containing machine-executable instructions 140. The machine-executable instructions 140 enable the processor 130 to control the operation and function of the magnetic resonance imaging system 100. The machine-executable instructions 140 may also enable the processor 130 to perform various data analysis and calculation functions. The computer memory 134 is further shown as containing pulse sequence commands 142. The pulse sequence commands are configured for controlling the magnetic resonance imaging system 100 to acquire magnetic resonance data from the subject 118 according to a magnetic resonance imaging protocol.

The memory 134 is further shown as containing magnetic resonance imaging data 144 that has been acquired by controlling the magnetic resonance imaging system 100 with the pulse sequence commands 142. The memory 134 is further shown as containing an MRI artifact detection module 146. The MRI artifact detection module 146 is implemented using at least one neural network. The memory 134 is further shown as containing a magnetic resonance image 148 that has been reconstructed from the magnetic resonance imaging data 144. The memory 134 is further shown as containing image metadata 150 that is descriptive of the magnetic resonance image 148. The image metadata 150 may contain such things as data descriptive of the pulse sequence commands 142 used to acquire the magnetic resonance imaging data 144. It may also contain data descriptive of the anatomy of the subject 118 that was imaged as well as other data descriptive of the subject 118 such as any implants, size, age or health status. The image metadata 150 may also contain information about the configuration or status of the magnetic resonance imaging system 100. The magnetic resonance image 148 and the image metadata 150 are used as input to the MM artifact detection module 146. The MRI artifact detection module 146 outputs a list of suggested pulse sequence command changes 152. For each of the members of the list 152 there is a corresponding image improvement likelihood score 154. This likelihood score 154 is a probability rating which is used to indicate how likely each of the members of the list 152 will improve the quality of the magnetic resonance image 148.

The memory 134 is shown as optionally containing a selection module 156. The selection module 156 applies a predetermined criteria to the likelihood scores 154 to select a selection 158 of a chosen pulse sequence command change from the list of suggested pulse sequence command changes 152. The selection 158 contains data which may be used to modify the pulse sequence commands 142. The memory 134 is shown as containing modified pulse sequence commands 160 that were created by modifying the pulse sequence commands 142 with the selection 158 of a chosen pulse sequence command change. The memory 134 is further shown as containing reacquired magnetic resonance imaging data 162. The reacquired magnetic resonance imaging data 162 was acquired by controlling the magnetic resonance imaging system with the modified pulse sequence commands 160. The memory 134 is further shown as containing a reacquired magnetic resonance image 164 that was reconstructed from the reacquired magnetic resonance imaging data 162.

Figure 2:
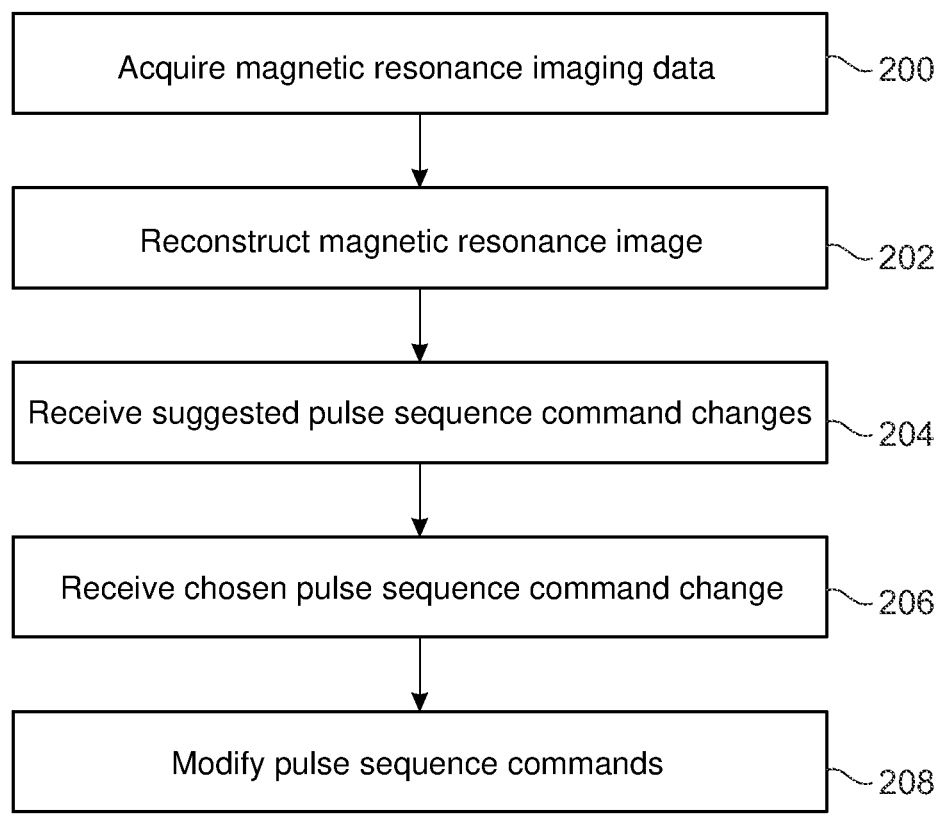
FIG. 2 shows a flow chart which illustrates a method of operating the magnetic resonance imaging system of FIG. 1.

FIG. 2 shows a flowchart which illustrates a method of operating the magnetic resonance imaging system 100 of FIG. 1. First in step 200 the magnetic resonance imaging system 100 is controlled with the pulse sequence commands 142 to acquire the magnetic resonance imaging data 144. Next in step 202 the magnetic resonance image 148 is reconstructed from the magnetic resonance imaging data 144. Then in step 204 the list of suggested pulse sequence command changes 152 is received from the MRI artifact detection module 146 by inputting the magnetic resonance image 148 and the image metadata 150 into it. Next in step 206 the selection 158 of a chosen pulse sequence command change is received. This for example may be achieved using the selection module 156. Finally, in step 208 the pulse sequence commands 142 are modified using the selection 158 of chosen pulse sequence commands.

Figure 3:
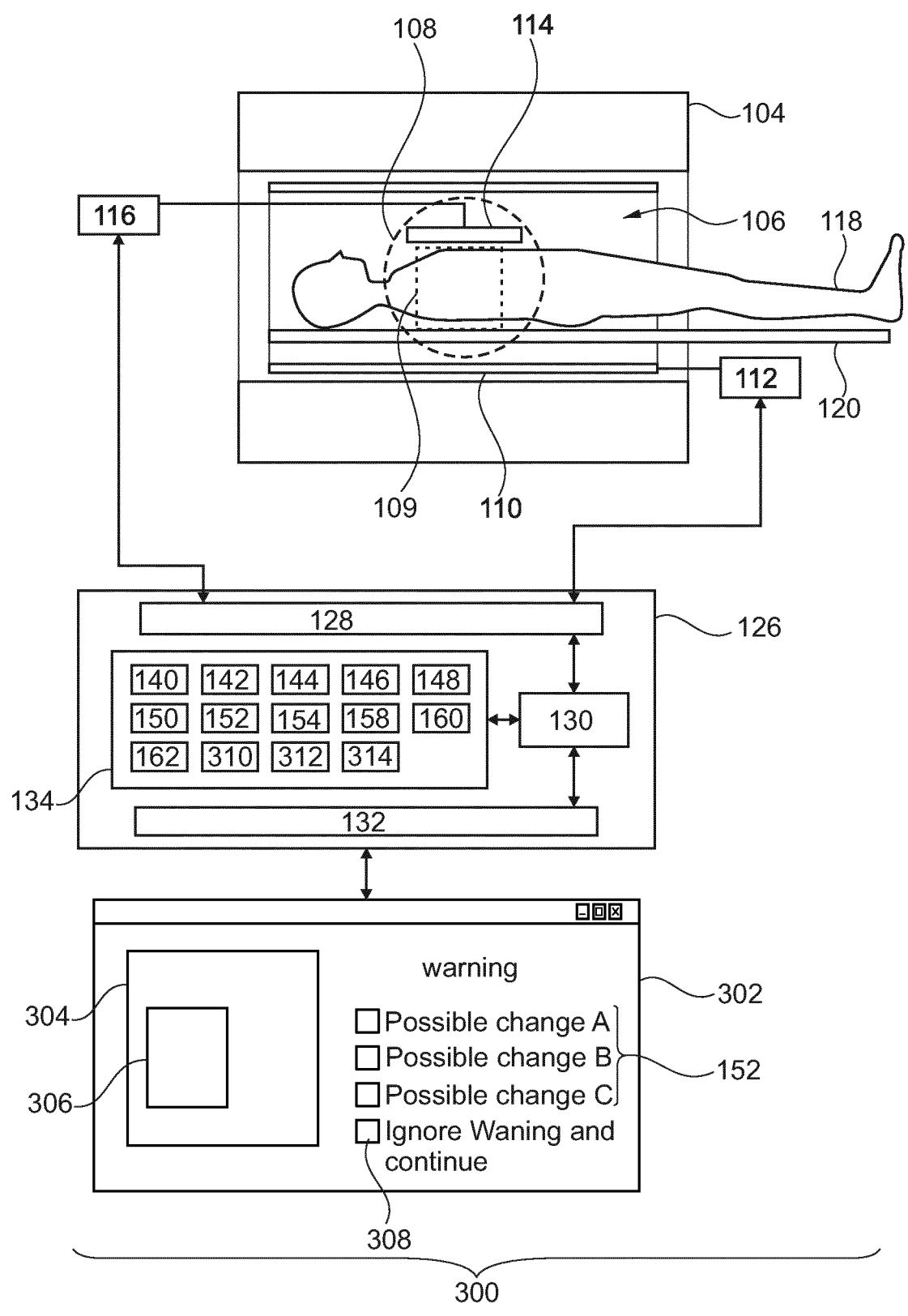
FIG. 3 illustrates a further example of a magnetic resonance imaging system.

FIG. 3 illustrates a further example of a magnetic resonance imaging system 300. The magnetic resonance imaging system 300 depicted in FIG. 3 is similar to the magnetic resonance imaging system 100 in FIG. 1 except the optional selection module 156 has been replaced with code that displays a warning prompt 302. The warning prompt 302 is shown as optionally rendering 304 the magnetic resonance image 148. The rendering 304 is also shown as having an artifact location indicator 306. In this case the artifact location indicator 306 is a bounding box that shows a region which likely contains an artifact. To the side of the rendering 304 is a list of suggested pulse sequence command changes 152. The operator is able to select one of these which then results in the processor 130 receiving the selection of a chosen pulse sequence command change 158. Below the list 152 is also a button 308 which enables the operator to ignore and continue without making a selection.

The memory 134 is shown as containing an optional training module 310. The optional training module 310 may for example be able to use deep learning or another method of training the one or more neural networks that are used to implement the MRI artifact detection module 146. The memory 134 is further shown as containing an optional log file 312. The optional log file 312 can be searched for magnetic resonance imaging protocols of images that have been labeled as being a failure. This may be useful for training. The memory 134 is further shown as containing an optional MRI artifact detection module database 314. For example, there could be multiple MRI artifact detection modules that have been trained. For example, the particular protocol that is chosen may be used for selecting the MRI artifact detection module 146 from the MRI artifact detection module database 314.

Figure 4:
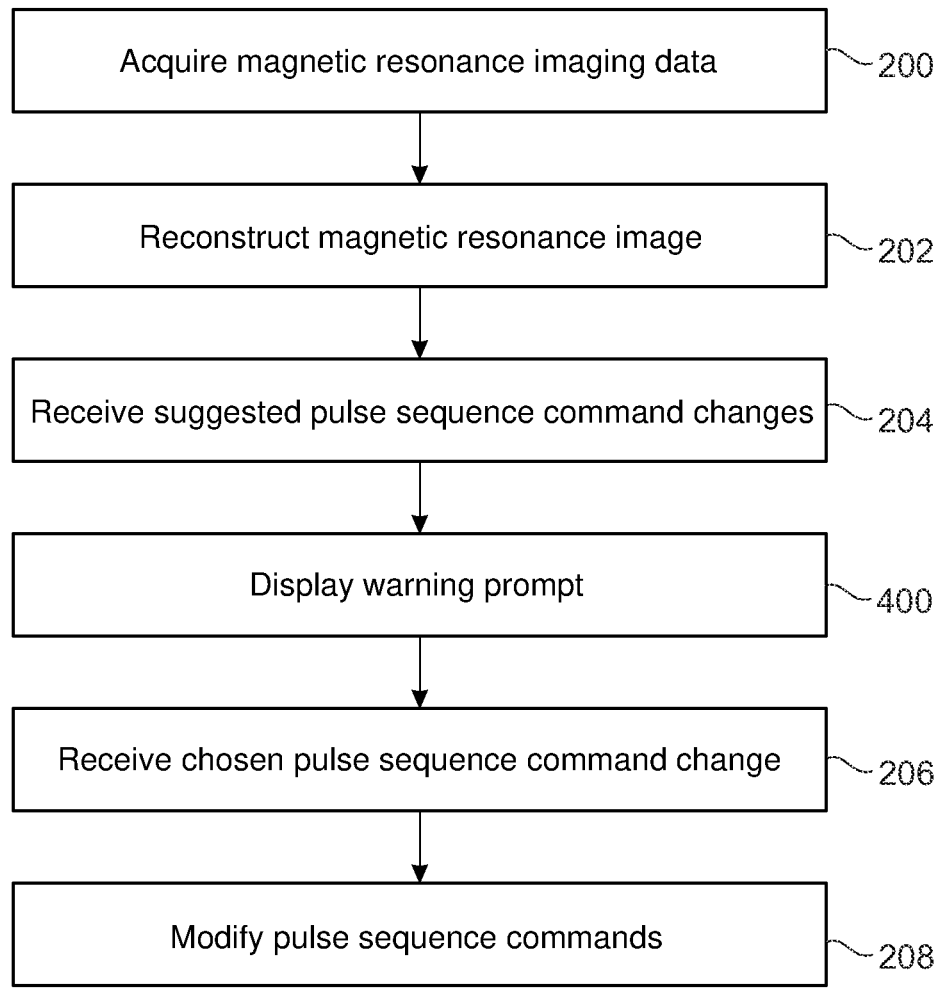
FIG. 4 shows a flow chart which illustrates a method of operating the magnetic resonance imaging system of FIG. 3.

FIG. 4 shows a flowchart which illustrates a method of operating the magnetic resonance imaging system 300 of FIG. 3. The method in FIG. 4 is similar to the method in FIG. 2. The method starts with steps 200, 202, and 204 as was performed in the method illustrated in FIG. 2. After step 204 the method proceeds to step 400. In step 400 a warning prompt 302 is displayed on the user interface 132 if at least one image improvement likelihood score 154 is above a predetermined threshold. The warning prompt displays the list 152 of the suggested pulse sequence command changes. After step 400 the method proceeds to step 206. In step 206 the selection of a chosen pulse sequence command change 158 is received from the warning prompt 302. After step 206 the method proceeds to step 208 as was illustrated in FIG. 2.

Figure 5:
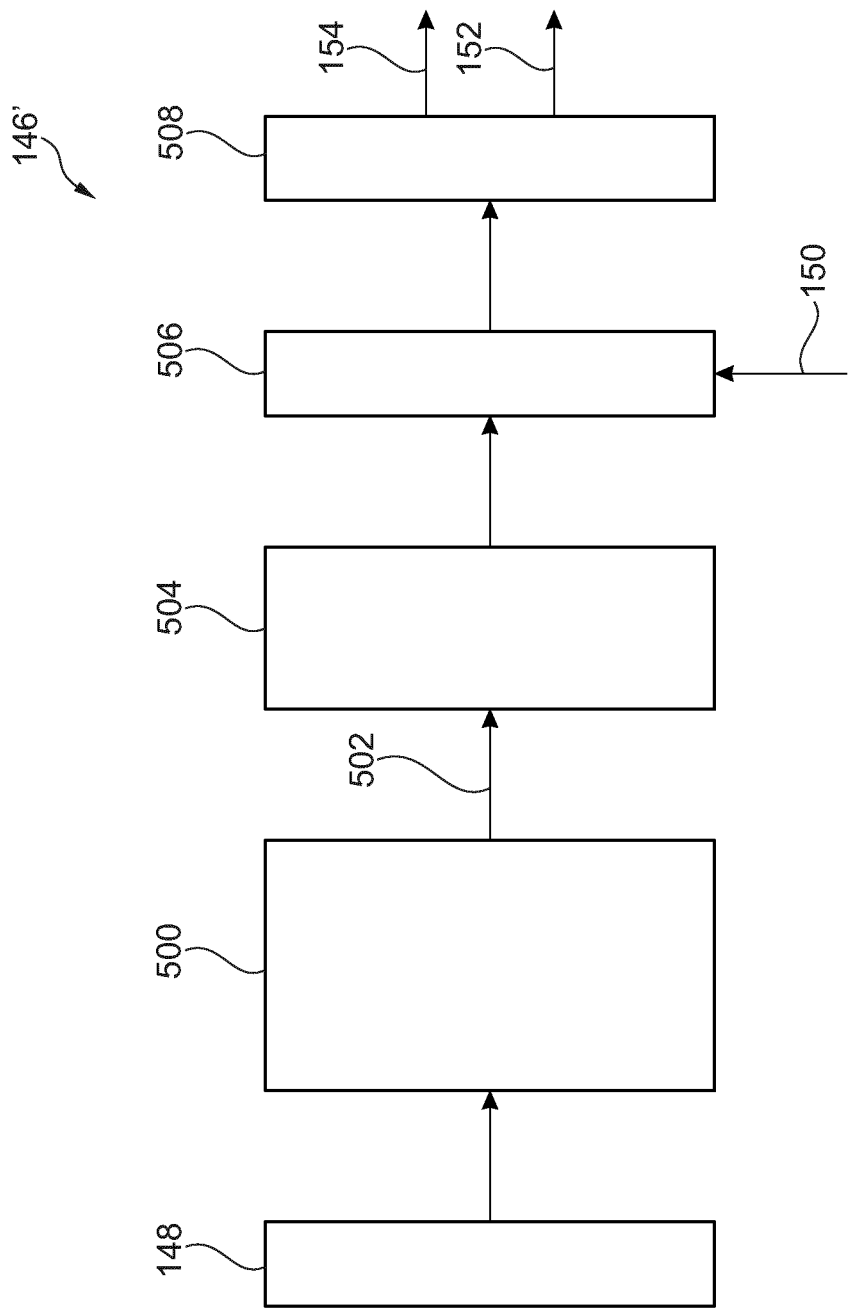
FIG. 5 illustrates an example of an MRI artifact detection module.

FIG. 5 illustrates an example of an implementation of an MRI artifact detection module 146'. In this example the MRI artifact detection module 146 comprises a single neural network. The neural network takes the magnetic resonance image 148 as input. This is input into a number of convolution layers 500. After the convolution layers there is a flattening process 502. After the flattening 502 there are then a number of fully connected layers 504, 506. Within these fully connected layers, layer 506 is shown as receiving the image Metadata 150 as input. As a practical matter the metadata can be input into any of these fully connected layers or the meta-data can also be split apart and input into different fully connected layers. After layer 506 there is an output 508 includes generation of a list of suggested pulse sequence commands 152 and for each of these an image improvement likelihood score 154. For example, the output 508 may contain a number of nodes for each of the possible suggested changes. The value at each of these outputs may be a probability that is equivalent to the image improvement likelihood score 154.

Figure 6:
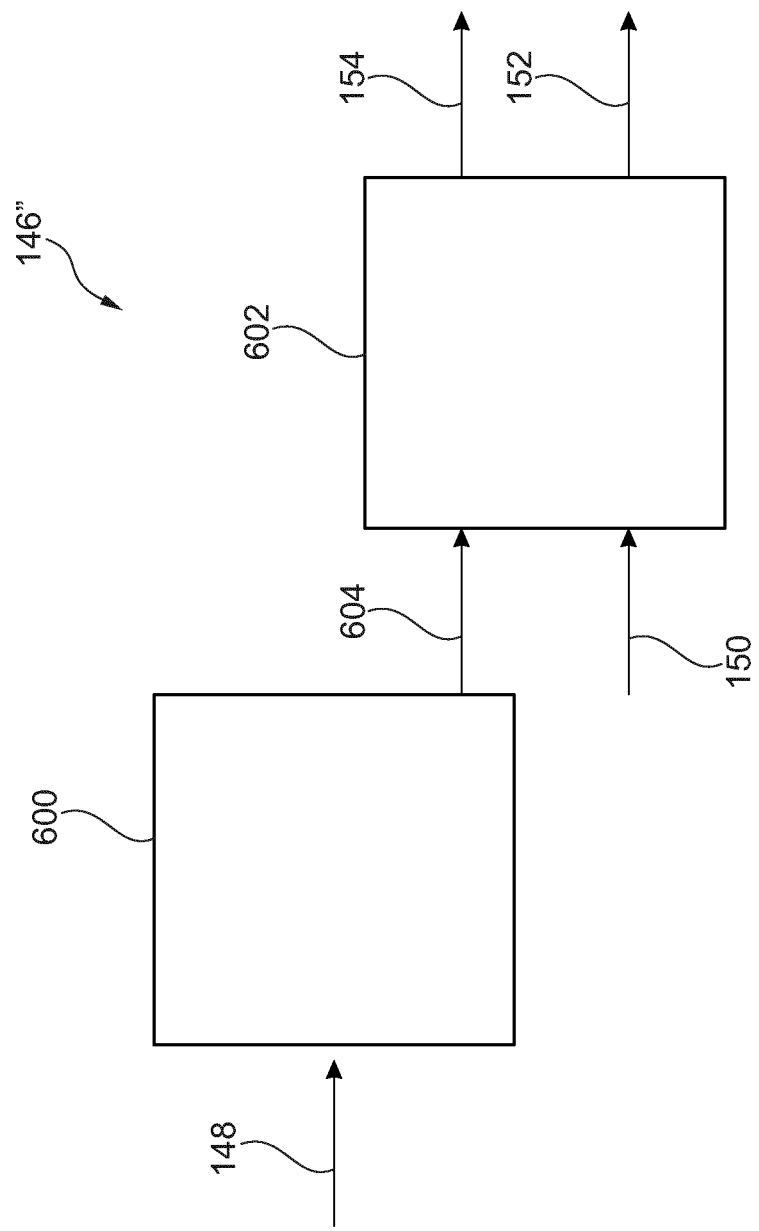
FIG. 6 illustrates a further example of an MRI artifact detection module.

FIG. 6 shows a further example of an implementation of an MRI artifact detection module 146". In this example there is a first neural network 600 and a pulse sequence modification module 602. The first neural network 600 takes the magnetic resonance image 148 as input and outputs an artifact classification 604. The artifact classification 604 and the image metadata 150 are then input into the pulse sequence modification module 602. The pulse sequence modification module 602 then outputs the list of suggested pulse sequence command changes 152 with each one of them having an image improvement likelihood score 154.

Artifacts in magnetic resonance imaging (MRI) are a frequent cause of image degradation (artifacts) in the clinical practice that may complicate the clinical workflow and render images unsuitable for diagnosis. A variety of specialized sequences and techniques have been developed to eliminate or suppress the different groups of artifacts. Successful application of these methods, however, requires that the operator is able to correctly detect and identify the artifacts present in the already acquired images.

Examples may provide for a software tool that realizes a fast and automatic assessment of previously acquired images to identify potential artifacts and propose suitable sequences to improve image quality.

In a first step in some examples, a deep convolutional neural network (an MRI artifact detection module that comprises at least one neural network) is trained using a large set of artifact-corrupted MR images and corresponding labels that define a suitable MR technique to improve image quality. In a second step, the software tool is applied to clinical images directly after data acquisition for automatic recommendation of suitable MR techniques to improve image quality in case artifacts have been detected.

The proposed software tool hence facilitates the acquisition of high-quality MR images while requiring less experience on the part of the operator, thereby improving the adoption of new MRI techniques in the clinical practice.

Image degradation due to artifacts is a common problem in the clinical application of magnetic resonance imaging (MRI). While experienced radiologists are sometimes able to "see through" these artifacts, corruption of the images if often so severe that medical diagnosis is impossible.

On the other hand, a variety of techniques have been proposed to reduce or eliminate image artifacts in MRI. While no general solution exists, many methods have been shown to be successful for particular types of artifacts. Examples include Metal Artifact Reduction for Orthopedic Implants (O-MAR) or MultiVane XD for the reduction of artifacts due to patient motion.

Correct detection and identification of artifacts in the clinical routine is a challenging task for the operator. In addition, once a particular type of artifact has been observed, selection of the appropriate scan technique to improve image quality can be difficult.

Technologists are often under time pressure and/or may lack the required experience to detect and avoid artifacts. Furthermore, introduction of new scan techniques that aim to avoid specific types of artifacts require comprehensive training of all radiology staff members that operate the MR scanner(s). These challenges may lead to poor adoption of new scan techniques that improve image quality.

Examples may provide for a software tool that allows for automatic detection of image artifacts and subsequent recommendation of suitable MR techniques to improve image quality. Since no input is required on part of the operator, the tool can be executed as a background process that only provides recommendations in case of detected artifacts and is otherwise invisible to the user. It relies on the training of a customized deep convolutional neural network (CNN) using a large number of artifact-corrupted MR images as well as corresponding image labels that define the most promising MR technique to eliminate the artifacts.

A schematic overview of one implementation of the proposed software tool is detailed below FIG. 7 as a workflow. The central component is a deep convolutional neural network 708. The optimal topology of the network depends on the details of the application scenario: Depending on the complexity (e.g., the number of artifact types that shall be detectable) and the characteristics (e.g., the spatial extent of the artifacts) of the desired application, different hyper-parameters of the CNN such as spatial size of the filters, number of filters, depth of the network, etc. can be chosen.

Figure 7:
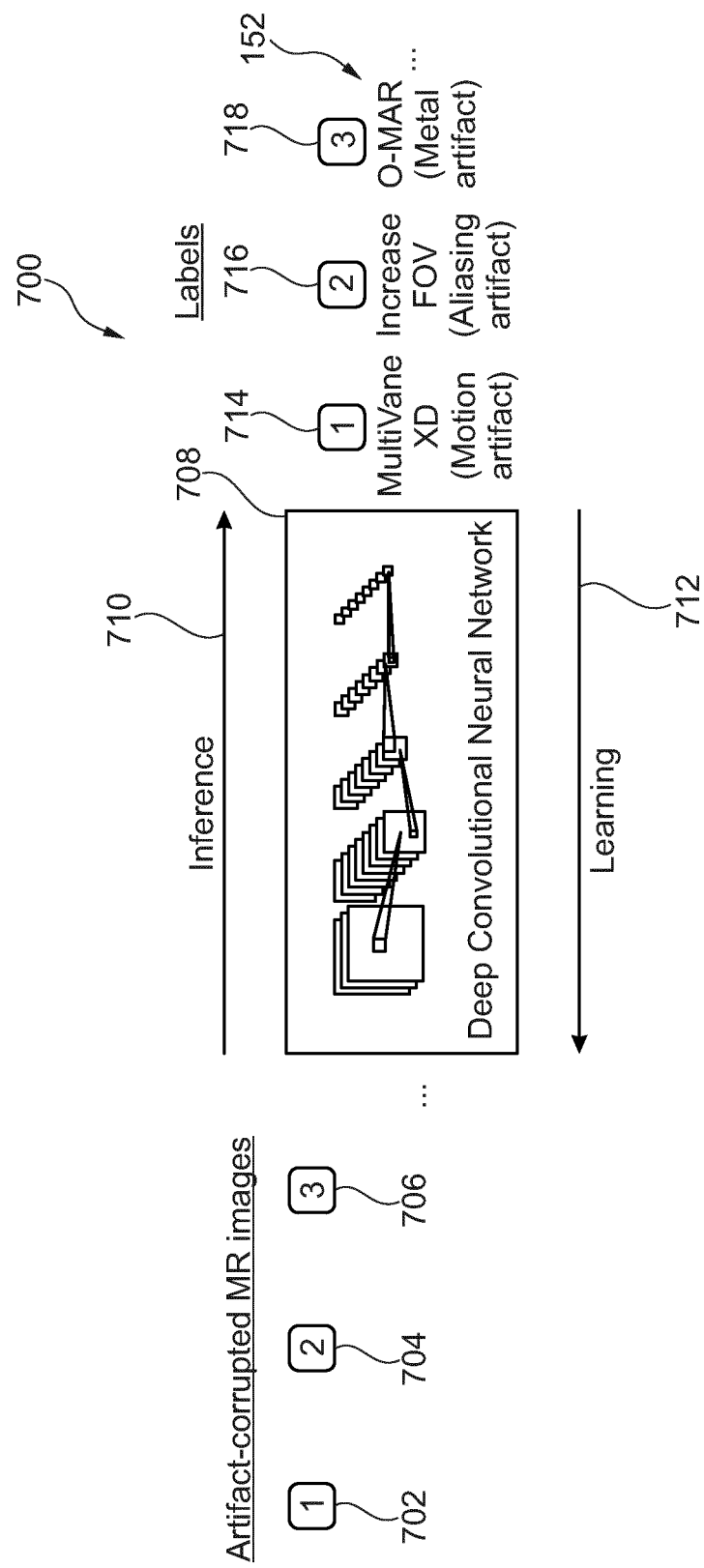
FIG. 7 illustrates an example of a workflow.

In the example illustrated in FIG. 7, the boxes labeled 702, 704, and 706 represent magnetic resonance images with artifacts that have corrupted them. There is a deep convolutional neural network 708 that is used to perform inference 710 and also may be trained using deep learning 712. The output of the deep convolutional neural network 708 are labels that are assigned to each of the images 702, 704, and 706. The label 714 corresponds to image 702. The label 716 corresponds to image 704. The label 718 corresponds to the image 706. Label 714 corresponds to a motion artifact. The label 716 corresponds to an aliasing artifact 716. The label 718 corresponds to a metal artifact 718. For each of these labels 714, 716, 718 there is a recommended pulse sequence command change. For label 714 the use of a MultiVane XD pulse sequence is suggested. For label 716 an increase in the field of view is suggested. For label 718 the use of an O-MAR protocol is suggested.

During training, various artifact-corrupted images 702, 704, 706 along with the corresponding labels are presented to the convolutional neural network 708. The labels define both the artifact as well as the most suitable MR technique to improve image quality. Once the network is fully trained, the network is capable of determining the most suitable artifact-avoiding MR technique without labels.

During the training stage, the parameters of the convolutional neural network (weights and biases) are optimized using established techniques such as stochastic gradient descent to achieve the desired automatic detection and recommendation capabilities. This is realized using a training set of artifact-corrupted MR images with corresponding labels that define the most promising MR technique to avoid these artifacts. In general, the quality of this training set, i.e. the validity of the labels is crucial for a successful optimization.

To generate such high-quality training datasets, a suitable database (e.g., a radiology department's image archive) may be searched for patient exams where a re-scan was performed due to artifact-related image degradation. In case image quality could be improved in the re-scan by application of a particular MR technique, the artifact-corrupted images are combined with the corresponding label (identifier of the MR technique) and added to the training set. To facilitate this procedure, manual tags that define the type of artifact as well as the artifact-preventing MR technique can be added to appropriate patient exams directly after data acquisition.

If such a procedure is not possible, e.g. due to lack of access to a suitable database, the training dataset may also be created using computational methods. This may be realized using a dedicated MR image simulation framework, which requires tissue properties such proton density, T1 and T2 values, etc. as input data to solve the governing Bloch equations. To allow for the generation of a large set of artifact-corrupted images, quantitative MR methods may be employed that map the required tissue properties. The corresponding artifact-avoiding MR techniques may then be retrieved from a simple look-up table to generate the labels. Alternatively, the artifact-preventing MR techniques can also be included in the simulation framework, thereby allowing for a more reliable prediction of the techniques' ability to improve image quality. The most successful MR technique is then combined with the image containing the simulated artifacts and added to the training set.

During the application stage, the trained CNN is used as an automatic image analysis tool that suggests suitable MR techniques to reduce artifact levels. It may be realized as a tailored monitoring software that detects artifacts and produces recommendations directly after data acquisition, thereby offering support to the operator to improve image quality in subsequent scans. The operator can decide whether to exchange a scan in the protocol with the proposed sequence. Alternatively, it may be applied to the archive of an imaging department to predict overall improvements in image quality that may be achieved if additional artifact-preventing MR techniques are introduced into the clinical workflow.

In contrast to conventional image processing methods, the application of a neural network also allows for a fine-tuning of the software even after deployment: feedback from the operators (e.g. collected by a pop-up window) can be used as input for a re-training stage, where the accuracy of the network is further optimized. This way, both sensitivity and specificity of the artifact detection as well as accuracy of the predicted (improved) image quality for the proposed MR technique may be further improved during the clinical application.

In one example the training dataset is generated using a large set of patient or volunteer images that contain a variety of relevant artifacts, which are manually labeled by an experienced radiologist or technologist based on his/her experience of preventing artifacts in the clinical practice. This approach may be suitable if the image archive does not contain sufficient re-scans to extract the required information, and if a comprehensive MR simulation framework is not available.

Examples may also use intra-scan analysis. In many common MR scans (e.g. multi-slice acquisition) images of the current scan can be and are already reconstructed while further data/slices are acquired. Such images are frequently displayed in a preview window (e.g. Philips "Autoview"). In one embodiment, such images are assessed as soon as they are reconstructed, and if artifacts are detected the operator is notified immediately with a proposal to stop the current acquisition and to run a proposed protocol instead.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
126 computer system
128 hardware interface
130 processor
132 user interface
134 computer memory
140 machine executable instructions
142 pulse sequence commands
144 magnetic resonance imaging data
146 MRI artifact detection module
146' MRI artifact detection module
146" MRI artifact detection module
148 magnetic resonance image
150 image metadata
152 list of suggested pulse sequence command changes
154 image improvement likelihood scores 156 selection module
158 selection of a chosen pulse sequence command change
160 modified pulse sequence commands
162 reacquired magnetic resonance imaging data
164 reacquired magnetic resonance image
200 control the magnetic resonance imaging system to acquire the magnetic resonance imaging data using the pulse sequence commands
202 reconstruct a magnetic resonance image using the magnetic resonance imaging data
204 receive a list of suggested pulse sequence command changes by inputting the magnetic resonance image and image metadata into an MRI artifact detection module
206 receive a selection of a chosen pulse sequence command change from the list of suggested pulse sequence command changes
208 modify the pulse sequence commands using the chosen pulse sequence command change
300 magnetic resonance imaging system
302 warning prompt
304 rendering of magnetic resonance image
306 anomaly location indicator
308 ignore and continue selector
310 training module
312 log file
314 MRI anomaly detection module database
400 display a warning prompt on a user interface if at least one image improvement likelihood score is above a predetermined threshold
500 convolution layers
502 flattening
504 fully connected layers
506 fully connected layer
508 output
600 first neural network
602 pulse sequence modification module
604 artifact classification
700 workflow
702 artifact corrupted MRI image
704 artifact corrupted MRI image
706 artifact corrupted MRI image
708 Deep Convolution Neural Network
710 Inference
712 Training
714 Label
716 Label
718 Label

The invention claimed is:

1. A magnetic resonance imaging system configured for acquiring magnetic resonance imaging data from a subject within an imaging zone, wherein the magnetic resonance imaging system comprises:
a memory configured to store machine executable instructions and pulse sequence commands, wherein the pulse sequence commands are configured to control the magnetic resonance imaging system to acquire magnetic resonance imaging data according to a magnetic resonance imaging protocol;
a processor configured to control the magnetic resonance imaging system, wherein execution of the machine executable instructions causes the processor to:
control acquisition of the magnetic resonance imaging data using the pulse sequence commands;
reconstruct a magnetic resonance image using the magnetic resonance imaging data;
input the magnetic resonance image and image metadata into an MRI artifact detection module, wherein the MRI artifact detection module comprises at least one neural network;
receive a list of suggested pulse sequence command changes by for changing the pulse sequence commands output by the MRI artifact detection module in response to the magnetic resonance image and the image metadata, wherein the image metadata comprises pulse sequence parameters selected from the pulse sequence commands, wherein each of the suggested pulse sequence command changes comprises an image improvement likelihood score associated with the suggested pulse sequence command change, wherein the at least one neural network has been trained using images from failed magnetic resonance imaging protocols and/or magnetic resonance data extracted from the magnetic resonance imaging protocols labeled as failed accessed from a log file which logs execution of previous magnetic resonance imaging protocols;
receive a selection of a chosen pulse sequence command change from the list of suggested pulse sequence command changes; and
modify the pulse sequence commands using the chosen pulse sequence command change.

2. A non-transitory computer readable medium storing machine executable instructions that, when executed by a processor, cause the processor to:
receive a magnetic resonance image;
receive image metadata corresponding to the magnetic resonance image, the image metadata comprising pulse sequence parameters selected from pulse sequence commands used to acquire the magnetic resonance image;
input the magnetic resonance image and the image metadata into at least one neural network; and
receive a list of suggested pulse sequence command changes output by the at least one neural network in response to the magnetic resonance image and the image metadata, wherein the at least one neural network is trained using images from failed magnetic resonance imaging protocols and/or magnetic resonance data extracted from the magnetic resonance imaging protocols labeled as failed accessed from a log file which logs execution of previous magnetic resonance imaging protocols, wherein each of the suggested pulse sequence command changes comprises an associated image improvement likelihood score, wherein the image improvement likelihood score represents a probability that the suggested pulse sequence command change will reduce artifacts of the magnetic resonance image; and
modify the pulse sequence commands using a selected one of the suggested pulse sequence command changes.

3. A method of operating a magnetic resonance imaging system configured for acquiring magnetic resonance imaging data from a subject within an imaging zone, the method comprising:
controlling the magnetic resonance imaging system to acquire the magnetic resonance imaging data using pulse sequence commands according to a magnetic resonance imaging protocol;
reconstructing a magnetic resonance image using the magnetic resonance imaging data;

input the magnetic resonance image and image metadata into at least one neural network;

receiving a list of suggested pulse sequence command changes output by the at least one neural network, wherein the at least one neural network is trained using images from failed magnetic resonance imaging protocols and/or magnetic resonance data extracted from the magnetic resonance imaging protocols labeled as failed accessed from a log file which logs execution of previous magnetic resonance imaging protocols, wherein the image metadata comprises pulse sequence parameters selected from the pulse sequence commands, wherein each of the suggested pulse sequence command changes comprises an associated image improvement likelihood score representing a probability that the suggested pulse sequence command change will reduce artifacts of the magnetic resonance image;

receiving a selection of a chosen pulse sequence command change from the list of suggested pulse sequence command changes; and modifying the pulse sequence commands using the chosen pulse sequence command change.

4. The magnetic resonance imaging system of claim 1, wherein execution of the machine executable instructions further causes the processor to:

search the log file for the magnetic resonance imaging protocols labeled as failed; and train the at least one neural network using images from the failed magnetic resonance imaging protocols and/or magnetic resonance data extracted from the magnetic resonance imaging protocols labeled as failed accessed from the log file.

5. The magnetic resonance imaging system of claim 1, wherein execution of the machine executable instructions further causes the processor to:

display a review prompt and the magnetic resonance image on a user interface, wherein the review prompt displays an artifact type listing;

receive a selection from the artifact type listing; and train the at least one neural network using the selection from the artifact type listing.

6. The magnetic resonance imaging system of claim 5, wherein execution of the machine executable instructions further causes the processor to:

provide a localization marking tool on the review prompt for the magnetic resonance image;

receive a localization selection indicating at least a portion of the magnetic resonance image;

receive an artifact location indicator from the MRI artifact detection module in response to the magnetic resonance image and the image metadata;

train the at least one neural network to generate the artifact location indicator using the localization selection;

display the magnetic resonance image on a warning prompt; and display the artifact location indicator superimposed on the magnetic resonance image on the warning prompt.

7. The magnetic resonance imaging system of claim 1, wherein execution of the machine executable instructions further causes the processor to:

record manual changes in the pulse sequence commands when acquisition of the magnetic resonance imaging data is manually repeated;

receive an image quality rating descriptive of a repeated magnetic resonance imaging reconstructed from the manually repeated magnetic resonance imaging data; and train the at least one neural network using the manual changes in the pulse sequence commands when the image quality rating is above a predetermined threshold.

8. The magnetic resonance imaging system of claim 1, wherein execution of the machine executable instructions further causes the processor to receive subject data descriptive of the subject, wherein the training of the at least one neural network is supplemented using the subject data, wherein the image metadata comprises the subject data.

9. The magnetic resonance imaging system of claim 1 wherein the at least one neural network is a single neural network.

10. The magnetic resonance imaging system of claim 9, wherein the single neural network comprises at least one fully connected layer, and wherein the image metadata is input into the at least one fully connected layer.

11. The magnetic resonance imaging system of claim 1, wherein the MRI artifact detection module comprises an artifact classifier, wherein the artifact classifier is a first neural network, wherein the at least one neural network comprises the first neural network, wherein the first neural network is configured to output an artifact classification of the magnetic resonance image in response to inputting the magnetic resonance image, wherein the MRI artifact detection module further comprises a pulse sequence modification module configured to output the list of suggested pulse sequence command changes in response to the artifact classification and the pulse sequence parameters selected from the pulse sequence commands.

12. The magnetic resonance imaging system of claim 11, wherein the pulse sequence modification module is a second neural network, an expert system, or a statistical learning module.

13. The magnetic resonance imaging system of claim 1, wherein the memory comprises an MRI artifact detection module database comprising multiple MM artifact detection modules, wherein the multiple MRI artifact detection modules comprise the MM artifact detection module, wherein execution of the machine executable instructions further causes the processor to select the MRI artifact detection module using the magnetic resonance imaging protocol.

14. The magnetic resonance imaging system of claim 1, wherein the image metadata further comprises one or more of system data descriptive of a state and/or a configuration of the magnetic resonance imaging system, and subject data descriptive of a physical condition of the subject.

15. The magnetic resonance imaging system of claim 1, wherein execution of the machine executable instructions further cause the processor to receive selection criteria from a selection module that is configured to select the chosen pulse sequence command change using a predetermined criteria applied to the image improvement likelihood score, execution of the machine executable instructions further causes the processor to display a warning prompt on a user interface if at least one image improvement likelihood score is above a predetermined threshold, wherein the warning prompt displays a list of the suggested pulse sequence command changes, and wherein the selection of the chosen pulse sequence command change is received from the user interface.

16. The magnetic resonance imaging system of claim 1, wherein execution of the machine executable instructions further causes the processor to display a warning prompt on a user interface when at least one image improvement likelihood score is above a predetermined threshold, wherein the warning prompt displays a list of the suggested pulse sequence command changes, and wherein the selection of the chosen pulse sequence command change is received from the user interface.

17. The non-transitory computer readable medium of claim 2, wherein execution of the machine executable instructions further causes the processor to:
   search the log file for the magnetic resonance imaging protocols labeled as failed; and
   train the at least one neural network using images from the failed magnetic resonance imaging protocols and/or magnetic resonance data extracted from the magnetic resonance imaging protocols labeled as failed accessed from the log file.

18. The non-transitory computer readable medium of claim 2 wherein execution of the machine executable instructions further causes the processor to:
   display a review prompt and the magnetic resonance image on a user interface, wherein the review prompt displays an artifact type listing;
   receive a selection from the artifact type listing; and
   train the at least one neural network using the selection from the artifact type listing.

19. The non-transitory computer readable medium of claim 18, wherein execution of the machine executable instructions further causes the processor to:
   provide a localization marking tool on the review prompt for the magnetic resonance image;
   receive a localization selection indicating at least a portion of the magnetic resonance image;
   receive an artifact location indicator in response to the magnetic resonance image and the image metadata;
   train the at least one neural network to generate the artifact location indicator using the localization selection;
   display the magnetic resonance image on a warning prompt; and
   display the artifact location indicator superimposed on the magnetic resonance image on the warning prompt.

20. The non-transitory computer readable medium of claim 2, wherein the at least one neural network comprises a first neural network and a second neural network, wherein the first neural network is configured to output an artifact classification of the magnetic resonance image in response to inputting the magnetic resonance image, wherein the second neural network is configured to output the list of suggested pulse sequence command changes in response to the artifact classification and the pulse sequence parameters selected from the pulse sequence commands.

* * * * *